United States Patent [19]

Findeisen et al.

[11] Patent Number: 5,041,551
[45] Date of Patent: Aug. 20, 1991

[54] PROCESS AND INTERMEDIATES FOR THE PREPARATION OF TRIAZOLONE DERIVATIVES

[75] Inventors: Kurt Findeisen, Odenthal; Markus Lindig, Hilden, both of Fed. Rep. of Germany

[73] Assignee: Bayer Aktiengesellschaft, Leverkusen, Fed. Rep. of Germany

[21] Appl. No.: 519,074

[22] Filed: May 4, 1990

[30] Foreign Application Priority Data

May 18, 1989 [DE] Fed. Rep. of Germany ....... 3916207

[51] Int. Cl.$^5$ .............................................. C07D 249/12
[52] U.S. Cl. .................................................. 548/263.8
[58] Field of Search ...................................... 548/263.8

[56] References Cited

FOREIGN PATENT DOCUMENTS 1222068 8/1961 Fed. Rep. of Germany .
3316095 11/1983 Fed. Rep. of Germany .
0305844 3/1989 Fed. Rep. of Germany .

OTHER PUBLICATIONS

Dobosz et al. I, "Reaction of Amionoguanidine, etc.", CA 99:212464y (1983).
Dobosz et al. II, "Reaction of Amionoguanidine, etc.", CA 99:212465z (1983).
Hirabayashi et al., "Thermally Developable, etc.", CA 100:183238j (1984).
J. Heterocycl. Chem. 15 (1978) 377-384.
Eur. J. Med. Chem-Chim. Ther., 1983-18, No. 3, pp. 215-220 (1982).

Primary Examiner—Mary C. Lee
Assistant Examiner—Patricia L. Morris
Attorney, Agent, or Firm—Sprung Horn Kramer & Woods

[57] ABSTRACT

Triazolone derivatives of the formula

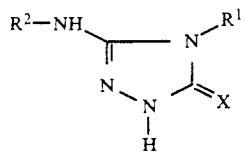

in which
 $R^1$ and $R^2$ each independently represents alkyl, alkenyl, alkynyl, halogenoalkyl, halogenoalkenyl, halogenoalkynyl, alkoxyalkyl, cycloalkylalkyl, cycloalkyl or represents aralkyl or aryl, which may be substituted
 $R^2$ also represents heteroaryl which may be substituted and
 X represents oxygen or sulphur, are obtained in good yields and at high purity by reacting an iso(thio)-cyanate of the formula

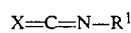

if desired in the presence of a diluent, with an aminoguanidine of the formula

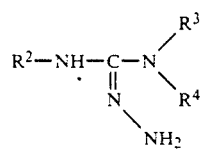

in which
 $R^3$ and $R^4$, independently of one another, represent alkyl, or with acid adducts thereof to form a (thio)ureidoguanidine of the formula

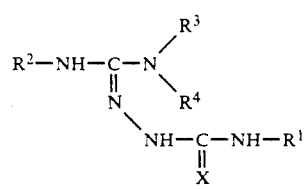

followed by condensation with elimination of dialkylamine ($HNR^3R^4$) to form the triazolone derivative and new (thio)ureidoguanidines.

7 Claims, No Drawings

PROCESS AND INTERMEDIATES FOR THE PREPARATION OF TRIAZOLONE DERIVATIVES

The invention relates to a novel process and novel intermediates for the preparation of substantially known triazolone derivatives.

It is known that 4-methyl-5-methylamino-2,4-dihydro-3H-1,2,4-triazol-3-thione is obtained as a byproduct of the reaction of 1,2-(bis-methylamino-thiocarbonyl) hydrazine with sodium acetate in an aqueous solution of ethanol (cf. J. Heterocycl. Chem. 15 (1978), 377-384).

It has now been found that triazolone derivatives of the general formula (I)

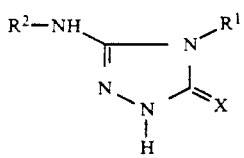

in which
- $R^1$ represents alkyl, alkenyl, alkynyl, halogenoalkyl, halogenoalkenyl, halogenoalkynyl, alkoxyalkyl, cycloalkylalkyl, cycloalkyl or represents aralkyl or aryl, each of which may be substituted if desired,
- $R^2$ represents alkyl, alkenyl, alkynyl, halogenoalkyl, halogenoalkenyl, halogenoalkynyl, alkoxyalkyl, cycloalkyl, cycloalkylalkyl or represents aryl, aralkyl or heteroaryl, each of which may be substituted if desired and
- X represents oxygen or sulphur, are obtained in good yields and at high purity, if iso(thio)cyanates of the general formula (II)

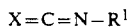

in which
- $R^1$ and X have the meanings given above, are reacted at temperatures of between 0° C. and 150° C. (step 1), if desired in the presence of a diluent, with aminoguanidines of the general formula (III)

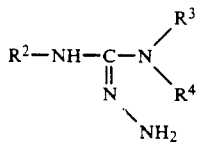

in which
- $R^2$ has the meaning given above and
- $R^3$ and $R^4$, independently of one another, represent alkyl, or with acid adducts of compounds of the formula (III) to form (thio)ureidoguanidines of the general formula (IV)

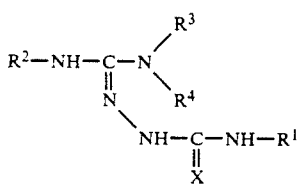

in which $R^1$, $R^2$, $R^3$, $R^4$ and X have the meanings given above, or, if desired, acid adducts of compounds of the formula (IV)

are if desired isolated by conventional methods or else without intermediate isolation ("in situ") and subjected to a further, condensation reaction, if desired in the presence of an acid acceptor and if desired in the presence of a diluent, at temperatures between 0° C. and 150° C. with elimination of a dialkylamine ($HNR^3R^4$) to form the compounds of the formula (I).

It must be considered surprising that by the process according to the invention virtually only the triazolone derivatives of the formula (I) are obtained as end products, with elimination of amines of the formula $HNR^3R^4$, since alternatively a ring closure of the intermediates of the formula (IV) with elimination of amines of the formula $R^2NH_2$ was also to be expected.

Advantages of the process according to the invention lie in the ready accessibility of the required starting materials, in the uncomplicated process control and in the good yield and the high purity of the products.

The triazolone derivatives which are to be prepared by the process according to the invention are defined in general by the formula (I). Preferably, the process according to the invention is used to prepare compounds of the formula (I) in which $R^1$ represents alkyl having 1 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkynyl having 2 to 8 carbon atoms and 1 to 13 identical or different halogen atoms, and alkoxyalkyl, the individual alkyl components having in each case 1 to 6 carbon atoms and being straight-chain or branched in each case, represents cycloalkylalkyl or cycloalkyl each having 3 to 7 carbon atoms in the cycloalkyl component and if desired 1 to 6 carbon atoms in the straight-chain or branched alkyl component or represents aralkyl or aryl, each of which if desired may be singly or multiply substituted by identical or different substituents, and having in each case 6 to 10 carbon atoms in the aryl component and if desired 1 to 6 carbon atoms in the straight-chain or branched alkyl component, suitable aryl substituents being: halogen, cyano, nitro, and alkyl, alkoxy, alkylthio, halogenoalkyl, halogenoalkoxy or halogenoalkylthio, each of which may be straight-chain or branched, and having in each case 1 to 4 carbon atoms and if desired 1 to 9 identical or different halogen atoms, represents alkyl having 1 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl or halogenoalkynyl having in each case 2 to 8 carbon atoms and 1 to 15 or 13 alkoxyalkyl, each having 1 to 6 carbon atoms in the individual alkyl components and being straight-chain or branched in each case, represents cycloalkyl having 3 to 7 carbon atoms, represents cycloalkylalkyl having 3 to 7 carbon atoms in the cycloalkyl component and 1 to 6 carbon atoms in the alkyl component or represents aralkyl having 6 to 10 carbon atoms in the aryl component and 1 to 6 carbon atoms in the alkyl component, aryl having 6 to 10 carbon atoms or heteroaryl having 2 to 9 carbon atoms and 1 to 3 heteroatoms, in particular nitrogen, oxygen and-/or sulphur, and each of which may if desired be singly or multiply substituted by identical or different substituents, suitable substituents in each case being: halogen, cyano, nitro and in each case straight-chain or branched alkyl, alkoxy, alkylthio, halogenoalkyl, halogenoalkoxy or halogenoalkylthio, each having 1 to 4 carbon atoms and if desired 1 to 9 identical or different halogen atoms, and X represents oxygen or sulphur.

It is particularly preferable to prepare by the process according to the invention, compounds of the formula (I) in which R$^1$ represents methyl, ethyl, n- or iso-propyl, n-, iso-, sec- or tert-butyl, n- or iso-pentyl, n- or iso-hexyl, represents allyl, propargyl, methoxymethyl, represents straight-chain or branched halogenoalkyl having 1 to 4 carbon atoms and 1 to 9 identical or different halogen atoms, in particular fluorine, chlorine or bromine, represents cyclopentyl, cyclohexylmethyl, cyclohexylethyl or represents benzyl or phenyl, each of which may contain up to 3 substituents which may be identical or different, suitable substituents being: fluoro, chloro, bromo, cyano, nitro, methyl, ethyl, n- or iso-propyl, n-, iso-, sec- or tert-butyl, methoxy, ethoxy, methylthio, trifluoromethyl, trifluoromethoxy or trifluoromethylthio, R$^2$ represents methyl, ethyl, n- or iso-propyl, n-, iso-, sec- or tert-butyl, n- or iso-pentyl, allyl, propargyl, represents halogenoalkyl having 1 to 4 carbon atoms, halogenoalkenyl having 3 to 6 carbon atoms or halogenoalkynyl having 3 to 6 carbon atoms and in each case 1 to 9 identical or different halogen atoms, each of the former being straight chain or branched, represents methoxymethyl, methoxyethyl, represents cyclopropyl, cyclopropylmethyl, cyclopentyl, cyclohexyl, cyclohexylmethyl, cyclohexylethyl, cyclopentylmethyl or represents benzyl, phenylethyl or phenyl, each of which may contain up to 3 substituents which may be identical or different, suitable substituents in each case being: fluoro, chloro, bromo, cyano, nitro, methyl, ethyl, n- or iso-propyl n-, iso-, sec- or tert-butyl, methoxy, ethoxy, methylthio, trifluoromethyl, trifluoromethoxy or trifluoromethylthio, and X represents oxygen or sulphur.

It is very particularly preferable to be able to prepare the compounds of the formula (I) in which R$^1$ represents methyl, ethyl, n- or iso-propyl, R$^2$ represents methyl, ethyl, n- or iso-propyl, n-, iso-, sec- or tert-butyl or allyl and X represents oxygen or sulphur.

Apart from the compounds mentioned in the Preparation Examples the following compounds of the general formula (I) are mentioned in detail:

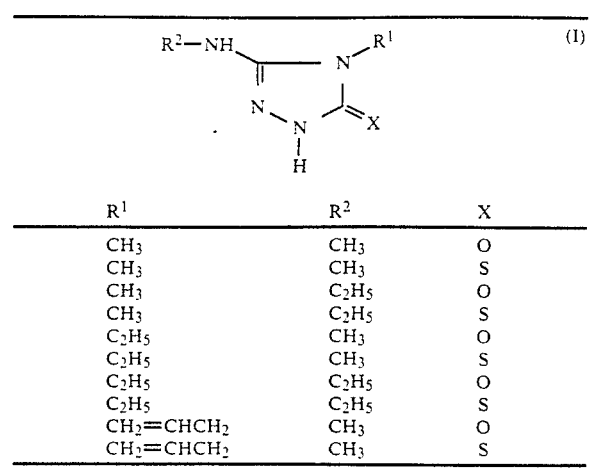

| R$^1$ | R$^2$ | X |
|---|---|---|
| CH$_3$ | CH$_3$ | O |
| CH$_3$ | CH$_3$ | S |
| CH$_3$ | C$_2$H$_5$ | O |
| CH$_3$ | C$_2$H$_5$ | S |
| C$_2$H$_5$ | CH$_3$ | O |
| C$_2$H$_5$ | CH$_3$ | S |
| C$_2$H$_5$ | C$_2$H$_5$ | O |
| C$_2$H$_5$ | C$_2$H$_5$ | S |
| CH$_2$=CHCH$_2$ | CH$_3$ | O |
| CH$_2$=CHCH$_2$ | CH$_3$ | S |

If for example 1-amino-2,2,3-trimethylguanidine hydrochloride and allyl isocyanate are used as starting materials, the course of the reaction in the process according to the invention can be represented by the following formula scheme:

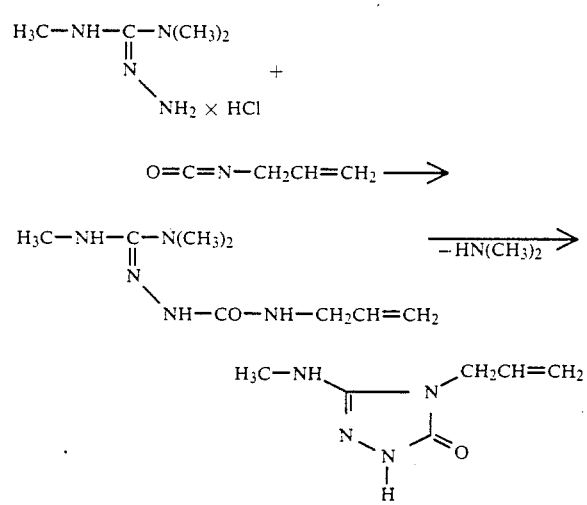

The iso(thio)cyanates which are to be used as starting materials in the process according to the invention for the preparation of compounds of the formula (I) are defined in general by the formula (II).

In formula (II), R$_2$ and X preferably or in particular have those meanings for R$_2$ and X which have already been quoted above as preferable or as particularly preferred in connection with the description of the compounds according to the invention of the formula (I).

The following examples of the starting materials of formula (II) may be mentioned: methyl, ethyl, propyl, isopropyl, butyl, isobutyl, sec-butyl, tert-butyl, pentyl, isopentyl, hexyl, isohexyl, allyl, propargyl, methoxymethyl, 2,2,2-trifluoroethyl, cyclopentyl, cyclohexyl, cyclopropyl, cyclopropylmethyl, cyclohexylmethyl and cyclohexylethyl isocyanate and isothiocyanate.

The starting materials of the formula (II) are known chemicals for organic syntheses.

The aminoguanidines which are further to be used as starting materials in the process according to the invention for the preparation of compounds of the formula (I) are defined in general by the formula (III).

In formula (III), $R^2$ preferably or in particular has that meaning which has already been quoted above as preferable or as particularly preferred for $R^2$ in connection with the description of the compounds according to the invention of the formula (I) and $R^3$ and $R^4$ preferably represent methyl or ethyl, particularly methyl.

The following examples may be mentioned as starting materials of the formula (III): 1-amino-2,2,3-trimethyl-, 1-amino-2,2-dimethyl-3-ethyl-, 1-amino-2,2-dimethyl-3-propyl-, 1-amino-2,2-dimethyl-3-isopropyl-, 1-amino-2,2-dimethyl-3dimethyl-3-isobutyl-, 1-amino-2,2-dimethyl-3-sec-butyl-, 1-amino-2,2-dimethyl-3-tert-butyl-, 1-amino-2,2-dimethyl-3-pentyl-, 1-amino-2,2-dimethyl-3dimethyl-3-allyl-, 1-amino-2,2-dimethyl-3-propargyl-, 1-amino-2,2-dimethyl-3-cyclopropyl-, 1-amino-2,2-di-methyl-3-cyclopropylmethyl-, 1-amino-2,2-di cyclopentyl-, 1-amino-2,2-dimethyl-3-cyclopentylmethyl-, 1-amino-2,2-dimethyl-3-cyclohexyl-, 1-amino-2,2-dimethyl-3-cyclohexylmethyl and 1-amino-2,2-dimethyl-3-cyclohexylethyl-guanidine, and the corresponding hydrochlorides.

The starting materials of the formula (III) or of the acid adducts thereof are known and/or can be prepared by processes known per se (cf. J. Org. Chem. 19 (1954), 1807; Bull. Soc. Chim. France 1975, 1649; EP-A 283,876).

The (thio)ureidoguanidines of the formula (IV) which can be isolated as intermediates in the process according to the invention are not yet known from the literature and are the subject of the present invention.

In formula (IV), $R^1$, $R^2$ and X preferably or in particular have those meanings for $R^1$, $R^2$ and X which have already been quoted above as preferable or as particularly preferred in connection with the description of the compound according to the invention of the formula (I) and $R^3$ and $R^4$ preferably represent methyl or ethyl, particularly methyl.

Apart from the compounds mentioned in the Preparation Examples, the following compounds of the general formula (IV) are mentioned in detail:

$$R^2-NH-C-N\begin{matrix}R^3\\ \diagdown\\ R^4\end{matrix} \quad (IV)$$
$$\underset{N}{\overset{\|}{\phantom{x}}}$$
$$\diagdown NH-C-NH-R^1$$
$$\overset{\|}{X}$$

| $R^1$ | $R^2$ | $R^3$ | $R^4$ | X |
|---|---|---|---|---|
| CH$_3$ | CH$_3$ | CH$_3$ | CH$_3$ | O |
| CH$_3$ | CH$_3$ | CH$_3$ | CH$_3$ | S |
| CH$_3$ | C$_2$H$_5$ | CH$_3$ | CH$_3$ | O |
| CH$_3$ | C$_2$H$_5$ | CH$_3$ | CH$_3$ | S |
| C$_2$H$_5$ | CH$_3$ | CH$_3$ | CH$_3$ | O |
| C$_2$H$_5$ | CH$_3$ | CH$_3$ | CH$_3$ | S |
| C$_2$H$_5$ | C$_2$H$_5$ | CH$_3$ | CH$_3$ | O |
| C$_2$H$_5$ | C$_2$H$_5$ | CH$_3$ | CH$_3$ | S |
| CH$_2$=CHCH$_2$ | CH$_3$ | CH$_3$ | CH$_3$ | O |
| CH$_2$=CHCH$_2$ | CH$_3$ | CH$_3$ | CH$_3$ | S |

Acid adducts in connection with the definition of the compounds of the formulae (III) and (IV) are understood to mean addition products of these compounds with acids, in particular with mineral acids such as hydrogen chloride, hydrogen bromide, hydrogen iodide and sulphuric acid.

The process according to the invention for the preparation of the compounds of formula (I) is preferably carried out using diluents. Virtually all inert organic solvents are suitable as diluents in the said process. These include preferably aliphatic and aromatic hydrocarbons, which may be halogenated if desired, such as pentane, hexane, heptane, cyclohexane, petroleum ether, naphtha, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as for example acetonitrile and propionitrile, amides such as for example dimethylformamide, dimethylacetamide and N-methylpyrrolidone, and dimethyl sulphoxide, tetramethylene sulphone and hexamethylphosphoryltriamide.

In the process according to the invention, all acid-binding agents which are usable conventionally for reactions of this type can be used as acid acceptors. Suitable acid acceptors are preferably alkali metal hydroxides such as for example sodium and potassium hydroxide, alkaline earth metal hydroxides such as for example calcium hydroxide, alkali metal (hydrogen) carbonates and alkali metal alcoholates such as sodium (hydrogen)carbonate, potassium (hydrogen)carbonate, sodium tert-butoxide and potassium tert-butoxide, and furthermore aliphatic, aromatic or heterocyclic amines, for example triethylamine, trimethylamine, dimethylaniline, dimethylbenzylamine, pyridine, 1,5-diazabicyclo[4.3.0]-non-5-ene (DBN), 1,8-diazabicyclo-[5.4.0]-undec-7-ene (DBU) and 1,4-diazabicyclo-[2.2.2]-octane (DABCO).

In the process according to the invention, the reaction temperatures can be varied within a relatively wide range. In general, the operation is carried out at temperatures of between 0° C. and 150° C., preferably at temperatures of between 10° C. and 120° C.

The process according to the invention is generally carried out at normal pressure However, it is also possible to operate under elevated or reduced pressure In order to carry out the process according to the invention, between 0.8 and 1.2 mol, preferably between 0.9 and 1.1 mol, of aminoguanidine of the formula (III) or an acid adduct thereof are generally used per 1 mol of iso(thio)cyanate of the formula (II).

Generally, the starting materials of the formulae (II) and (III) are admixed at room temperature or with slight cooling and then stirred, preferably at elevated temperature, until the reaction of the starting materials has virtually ended. The (thio)ureidoguanidines of the formula (IV) which generally occur in crystalline form, or the acid adducts thereof can be isolated by conventional methods, for example by filtering under suction. However, they can also be condensed without intermediate isolation ("in situ") to form compounds of the formula (I). For this purpose, an acid acceptor is preferably added to the reaction mixture and the mixture is stirred preferably at elevated temperature until elimination of the amine has ended.

Working-up can be carried out by conventional methods. Generally, the said reaction mixture is filtered hot and the product of the formula (I), which occurs in crystalline form when the filtrate is cooled, is isolated by filtering with suction. Alternatively, after the hot filtration, the filtrate is concentrated, the residue is shaken with water and with an organic solvent which is virtually immiscible in water, such as for example methylene chloride, and the organic phase is separated off, dried with a drying agent, such as for example sodium sulphate and filtered. The solvent is then carefully distilled off from the filtrate in vacuo. The residue remaining essentially contains the product of the formula (I).

The compounds of the formula (I) can for example be used as additives in the electroplating of copper (cf. JP 71-37,646 = JP 46-37,646, quoted in Chem. Abstracts 77 (1972), 147,067a).

The compounds of the formula (I) are also valuable intermediates for the preparation of herbicides of the formula (V)

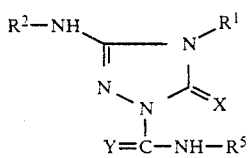

in which

R$^1$, R$^2$ and X have the meaning given above, R$^5$ represent hydrogen, alkyl, alkenyl, alkynyl, halogenoalkyl, halogenoalkenyl, halogenoalkynyl, cyano alkyl, hydroxyalkyl, alkoxyalkyl, alkylaminoalkyl, alkoximinoalkyl, alkoxycarbonylalkyl, alkoxycarbonylalkenyl, represent cycloalkyl, cycloalkylalkyl, cycloalkenyl or cycloalkenylalkyl, each of which may if desired be substituted, represent heterocyclylalkyl which may if desired substituted, represent aralkyl, aroyl or aryl, each of which may if desired be substituted, represent alkoxy, alkenyloxy, alkynyloxy, aralkyloxy or aryloxy, each of which may if desired be substituted and Y represents oxygen or sulphur.

The herbicidal compounds of the formula (V) are obtained if triazolone derivatives of the formula (I)

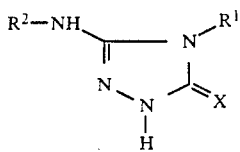

in which

R$^1$, R$^2$ and X have the meaning given above, are reacted with iso(thio)cyanates of the formula (VI),

R$^5$—N=C=Y (VI)

in which

R$^5$ and Y have the meanings given above, if desired in the presence of a diluent such as for example acetonitrile and if desired in the presence of a reaction auxiliary such as for example diazabicycloundecene (DBU) at temperatures of between 0° C. and +150° C.

PREPARATION EXAMPLES

EXAMPLE 1

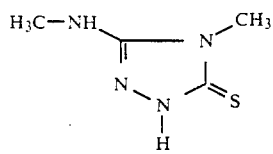

Step 1

21.9 g (0.3 mol) of methyl isothiocyanate are added to a mixture of 45.75 g (0.3 mol) of 1-amino-2,2,3trimethylguanidine hydrochloride and 300 ml of acetonitrile and the mixture is stirred for 2 hours at the reflux temperature. After cooling the product which has resulted in crystalline form is isolated by filtration with suction. 55.0 g (81 % of theory) are obtained of 1- o (methylamino-thiocarbonylamino)-2,2,3-trimethylguanidine hydrochloride of the formula given below.

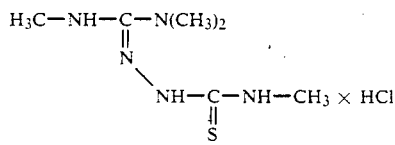

$^1$H-NMR(DMSO-D$_6$, δ, ppm): 2.80–2.82; 2.85–2.87; 2.95. MS: M=189.

Step 2

55.0 g (0.245 mol) of 1-(methylamino-thiocarbonylamino)-2,2,3-trimethylguanidinehydrochlorideare stirred in 300 ml of acetonitrile with 33.6 g (0.40 mol) of sodium hydrogencarbonate for 40 minutes at the reflux temperature. The mixture is then filtered at 70° C. and the product which has been crystallized out by cooling the filtrate and concentrating it to 1/4 of its volume is isolated by filtration with suction. 32 g (74 % of theory relative to the starting materials of Step 1 or 91 % of theory relative to the starting material of Step 2) are obtained of 4-methyl-5-methylamino-2,4-dihydro-3H-1,2,4-triazole-3-thione having a melting point of 213
$^1$H-NMR(DMSO-D$_6$, δ, ppm): 2.68–2.73; 3.27.
MS: M=44.

EXAMPLE 2

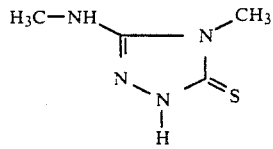

(one-pot process)

A mixture of 45.75 g (0.3 mol) of 1-amino-2,2,3trimethylguanidine hydrochloride, 21.9 g (0.3 mol) of methyl isothiocyanate and 300 ml of acetonitrile are stirred for 2 hours at the reflux temperature. After cooling to 40° C., 42 g (0.5 mol) of sodium hydrogencarbonate are added and the mixture is stirred for a further 40 minutes at the reflux temperature. The mixture is then filtered at 70° C. and the product which has been crystallized out by cooling the filtrate and concentrating it to 1/4 of its volume is isolated by filtration with suction. 33.6 g (78 % of theory) are obtained of 4-methyl-5-methylamino-2,4-dihydro-3H-1,2,4-tr having a melting point of 213° C.

EXAMPLE 3

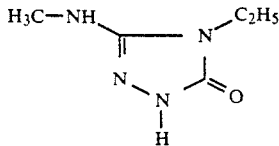

45.75 g (0.3 mol) of 1-amino-2,2,3-trimethylguanidine hydrochloride and 21.3 g (0.3 mol) of ethyl isocyanate are stirred in 300 ml of acetonitrile for 2 hours at the reflux temperature, and then cooled to 40° C., to this 50.4 g (0.6 mol) of sodium hydrogencarbonate are added and the mixture is stirred for a further 8 hours at the reflux temperature. In order to work up the batch, it is filtered hot and the filtrate is cooled. The precipitated reaction product is filtered off with suction, washed and dried.

25 g (59 % of theory) are obtained of 5-methylamino-4-ethyl-2,4-dihydro-3H-1,2,4-triazol-3-o a melting point of 208°-210° C.

EXAMPLE 4

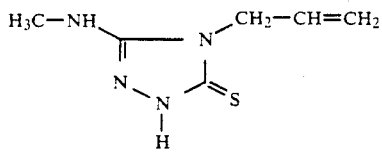

91.5 g (0.6 mol) of 1-amino-2,2,3-trimethylguanidine hydrochloride and 59.4 g (0.6 mol) of allyl isothiocyanate are stirred in 800 ml of acetonitrile for 2 hours at the reflux temperature, and then to this 60.6 g.(0.6 mol) of triethylamine are added dropwise, the mixture is stirred for a further hour at the reflux temperature, cooled, filtered, the filtrate concentrated and the oily residue partitioned between dichloromethane and water. The combined organic phases are dried over sodium sulphate and concentrated 68 g (67 % of theory) are obtained of 5-methylamino-4-allyl-2,4-dihydro-3H-1,2,4-triazole-3-having a melting point of 129°-131° C.

PREPARATION EXAMPLE FOR A HERBICIDAL COMPOUND OF THE FORMULA (V)

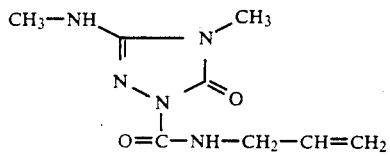

4.2 g (0.05 mol) of allyl isocyanate and 3 drops of diazabicycloundecene (DBU) are added to 6.4 g (0.05 mol) of 3-methylamino-4-methyl-(1H)-1,2,4-triazolin-5-one in 150 ml of acetonitrile, the temperature of the reaction mixture increasing to 30° C. The mixture is then stirred for 30 minutes at the reflux temperature, then concentrated in vacuo and recrystallized from ethyl acetate.

7,9 g (75 % of theory) are obtained of 1-allylaminocarbonyl-3-methylamino-4-methyl-1,2,4-triazolin5-one having a melting point of 136°-137° C.

What is claimed is:

1. A process for the preparation of a triazolone derivative of the formula

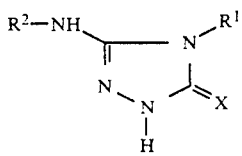

in which

R[1] represents alkyl having 1 to 8 carbon atoms, alkenyl having 2 to 8 carbon atoms, alkynyl having 2 to 8 carbon atoms, ahlogenoalkyl having 1 to 8 carbon atoms and 1 to 17 identical or different halogen atoms, halogenoalkenyl having 2 to 8 carbon atoms and 1 to 5 identical or different halogen atoms, halogenoalkynyl having 2 to 8 carbon atoms and 1 to 13 identical or different halogen atoms, and alkoxyalkyl, the individual alkyl components having in each case 1 to 6 carbon atoms and being straight-chain or branched in each case, represents cycloalkylalkyl or cycloalkyl each having 3 to 7 carbon atoms in the cycloalkyl component and 1 to 6 carbon atoms in the straight-chain or branched alkyl component or represents unsubstituted or substituted carbocyclic aralkyl or aryl, having in each case 6 to 10 carbon atoms in the aryl component and 1 to 6 carbon atoms in the straight-chain or branched alkyl component, the aryl substituents being selected from the group consisting of halogen, cyano, nitro, alkyl, alkoxy or alkylthio, each of which may be straight-chain or branched and having in each case 1 to 4 carbon atoms and halogenoalkyl, halogenoalkoxy or halogenoalkylthio, each of which may be straight-chain or branched, and having in each case 1 to 4 carbon atoms and 1 to 9 identical or different halogen atoms.

R[2] represents alkyl having 1 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl or halogenoalkynyl having in each case 2 to 8 carbon atoms and 1 to 15 identical or different halogen atoms, and alkoxyalkyl, each having 1 to 6 carbon atoms in the individual alkyl components and being straight-chain or branched in each case, cycloalkyl having 3 to 7 carbon atoms, cycloalkylalkyl having 3 to 7 carbon atoms in the cycloalkyl component and 1 to 6 carbon atoms in the alkyl component or aralkyl having 6 to 10 carbon atoms in the aryl component and 1 to 6 carbon atoms in the alkyl component, or aryl having 6 to 10 carbon atoms, which may be unsubstituted or substituted by identical or different substituents selected from the group consisting of halogen, cyano, nitro, $C_{1-4}$-alkyl, $C_{1-4}$-alkoxy, $C_{1-4}$-alkylthio or $C_{1-4}$-halogenoalkyl, $C_{1-4}$-halogenoalkoxy or $C_{1-4}$-halogenoalkylthio, each having 1 to 9 identical or different halogen atoms, and X represents oxygen or sulphur, comprising reacting an iso(thio) cyanate of the formula II $$X=C=N-R^1$$

with an aminoguanidine of the formula

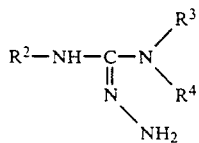

in which

R$^3$ and R$^4$, independently of one another, represent alkyl, or with an acid adduct thereof to form a (thio)ureidoguanidine of the formula

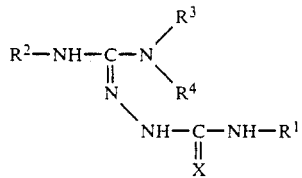

or an acid adduct thereof and condensing with elimination of a dialkylamine, HNR$^3$R$^4$, of the (thio)ureidoguanidine to form the triazolone derivative.

2. A process according to claim 1, wherein the reaction and condensation is carried out at temperatures between 0° C. and 150° C.

3. A process according to claim 1, wherein the reaction and condensation are carried out in the presence of a solvent.

4. A process according to claim 1, wherein the condensation reaction is carried out in the presence of an acid-binding agent selected from the group consisting of alkali metal hydroxides, alkaline earth metal hydroxides, alkali metal carbonates, hydrogen carbonates, alkali metal alcoholates, triethylamine, trimethylamine, dimethylaniline, dimethylbenzylamine, pyridine, 1,5-diazabicyclo[4.3.0]-non-5-ene (DBN), 1,8-diazabicyclo-[5.4.0]-undec-7-ene (DBU) and 1,4-diazabicyclo-[2.2.2]-octane.

5. A process according to claim 1, wherein 0.8 to 1.2 mol of aminoguanidine or an acid adduct thereof is used per 1 mol of iso(thio)cyanate.

6. A process according to claim 1, wherein the (thio)ureidoguanidine is isolated from the iso(thio)cyanate/aminoguanidine reaction mixture prior to condensation.

7. A process according to claim 1, wherein the reaction of iso(thio)cyanate/aminoguanidine and condensation are carried out as a one-pot process without isolation of the (thio)ureidoguanidine.

* * * * *

UNITED STATES PATENT AND TRADEMARK OFFICE
CERTIFICATE OF CORRECTION

PATENT NO. : 5,041,551

DATED : August 20, 1991

INVENTOR(S) : Findeisen et al.

It is certified that error appears in the above-identified patent and that said Letters Patent is hereby corrected as shown below:

Col. 10, line 20   Delete " ahlogenoalkyl " and substitute -- halogeno-alkyl --

Signed and Sealed this

Eighth Day of June, 1993

Attest:

MICHAEL K. KIRK

Attesting Officer

Acting Commissioner of Patents and Trademarks